United States Patent [19]

Schulte-Huermann et al.

[11] 4,261,918
[45] Apr. 14, 1981

[54] PROCESS FOR THE PREPARATION OF CHLOROFORMIC ACID METHYL ESTER

[75] Inventors: Werner Schulte-Huermann, Krefeld; Erhard Schellmann; Jurgen Lahrs, both of Cologne, all of Fed. Rep. of Germany

[73] Assignee: Bayer Aktiengesellschaft, Leverkusen, Fed. Rep. of Germany

[21] Appl. No.: 84,207

[22] Filed: Oct. 12, 1979

[30] Foreign Application Priority Data

Nov. 2, 1978 [DE] Fed. Rep. of Germany ....... 2847484

[51] Int. Cl.$^3$ .............................................. C07C 68/02
[52] U.S. Cl. .................................................... 260/463
[58] Field of Search ......................................... 260/463

[56] References Cited

U.S. PATENT DOCUMENTS 4,039,569  8/1977  Bell et al. ............................. 260/463

FOREIGN PATENT DOCUMENTS 2704262  11/1977  Fed. Rep. of Germany ....... 260/455 B Primary Examiner—John D. Randolph
Assistant Examiner—Robert C. Whittenbaugh
Attorney, Agent, or Firm—Sprung, Felfe, Horn, Lynch & Kramer

[57] ABSTRACT

In a process for the continuous preparation of chloroformic acid methyl ester by contacting phosgene with methanol at a temperature of up to 50° C. in a reactor which contains chloroformic acid methyl ester as the solvent and in which phosgene is dispersed, the improvement wherein gaseous phosgene is dispersed by already formed and circulated chloroformic acid methyl ester into the reaction chamber by means of a dispersing device, and at the same time methanol is introduced into the homogeneous gas-in-liquid dispersion.

4 Claims, 1 Drawing Figure

U.S. Patent    Apr. 14, 1981    4,261,918
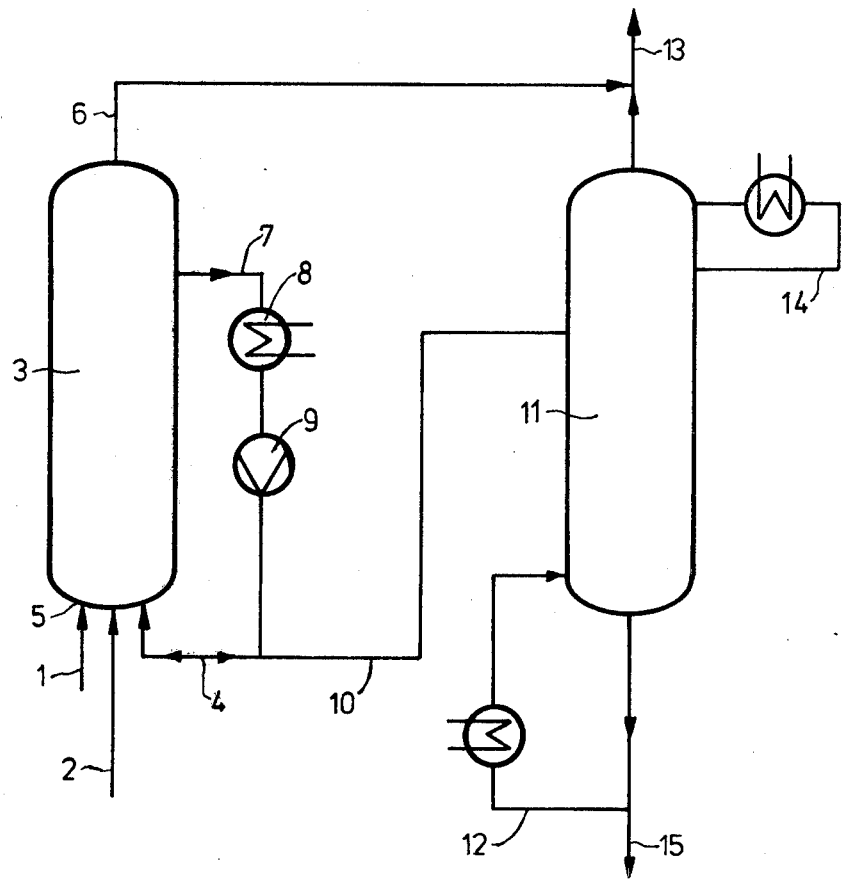

4,261,918

PROCESS FOR THE PREPARATION OF CHLOROFORMIC ACID METHYL ESTER

BACKGROUND OF THE INVENTION

1. Field of the Invention

The invention relates to a process for the preparation of chloroformic acid methyl ester by reacting phosgene with methanol.

2. Discussion of Prior Art

The preparation of chloroformic acid methyl ester by passing phosgene into methanol in the temperature range from 0° to 10° C. is known (Houben-Weyl, volume 8, 101 et seq., 1952).

German Offenlegungsschrift No. 2,251,206 describes the continuous preparation of chloroformic acid methyl ester, in which the alcohol and phosgene are fed, the alcohol preferably being fed by means of a spray nozzle, into a reaction vessel, which in momentary equilibrium contains at least 20% by weight of phosgene in the reaction mixture, in such a way that the time for homogeneously mixing the alcohol into the reaction mixture is less than 5 seconds, an amount of the reaction mixture corresponding to the amounts of alcohol and phosgene fed in is removed and is freed from phosgene and hydrogen chloride and the phosgene is recycled into the reaction vessel.

It is known from German Offenlegungsschrift No. 2,453,284 that in the preparation of chloroformic acid methyl ester, the time for homogeneously mixing in the alcohol is less than 1 second, whereupon in momentary equilibrium an excess of phosgene in the reaction mixture now only of at least 2% by weight, a temperature of up to 70° C. and a residence time of up to 300 minutes can be maintained.

According to the process described in German Offenlegungsschrift No. 2,704,262, for the preparation of chloroformic acid methyl ester, the liquid methanol is dispersed rapidly in the circulating chloroformic acid methyl ester (see pages 7 and 8). The phosgene is absorbed from the circulating reaction mixture in countercurrent in an absorption tower which is packed with glass Raschig rings or another packing material which does not have a catalytic action (page 8, lines 13 to 16). It is also stated (page 2, lines 2 to 3) that the liquid phosgene is dispersed in the chloroformic acid methyl ester.

SUMMARY OF INVENTION

A process has now been found for the continuous preparation of chloroformic acid methyl ester by reacting phosgene with methanol at a temperature of up to 50° C. in the reactor which contains chloroformic acid methyl ester as the solvent and in which phosgene is dispersed, characterized in that gaseous phosgene, together with any chloroformic acid methyl ester which has already formed, is dispersed in the reaction chamber by means of a spray nozzle, and at the same time methanol is introduced into the homogeneous gas-in-liquid dispersion.

Chloroformic acid methyl ester is generally prepared from methanol and an excess of phosgene in a cyclic process. Chloroformic acid methyl ester is initially introduced into the apparatus as the solvent. The essential components of the apparatus for this cycle are the reactor, the heat exchanger and the devices for adding and removing the reactants and the reaction products, namely chloroformic acid methyl ester and hydrogen chloride.

In the process according to the invention, the gaseous phosgene is finely dispersed in the reaction chamber by means of a spray nozzle, there being no time limit. At the same time, the methanol is introduced, in a finely divided form, into the gas-in-liquid dispersion. It is essential for the process according to the invention that a homogeneous gas-in-liquid dispersion of phosgene and the reaction mixture, essentially chloroformic acid methyl ester, as well as methanol, is formed in the reaction chamber.

The process according to the invention can be carried out in the temperature range usual for the preparation of chloroformic acid methyl ester from methanol and phosgene, preferably the range from 0° to 30° C. However, it is essential that during the process the reaction temperature in the reaction chamber rises by at most 10° C., preferably by at most 5° C., independently of the starting temperature. In the process according to the invention, the rise in temperature in the reaction chamber can be controlled by the amount of chloroformic acid methyl ester circulated. Control of the temperature within the limits according to the invention is preferably achieved when 1 mol of methanol is reacted with 1 to 1.3 mols, preferably 1 to 1.1 mols, of phosgene in 5 to 20 mols, preferably 10 to 15 mols, of chloroformic acid methyl ester as the solvent. The residue time of the reactants in the reaction zone preferably is 1 to 5 minutes.

The reaction chamber in the process according to the invention is preferably in the lower section of a bubble column, which is connected-on-downstream as a post-reaction chamber. Bubble columns which can be used for the process according to the invention are in themselves known (see Ullmann, (1972), volume 1, page 228 et seq.).

BRIEF DESCRIPTION OF DRAWING

Referring to the annexed drawing, the same in a flow diagram stowing vessels and for carrying out the process.

DESCRIPTION OF SPECIFIC EMBODIMENT

The process according to the invention can be carried out, for example, as illustrated with the aid of drawing: gaseous phosgene (1) is finely dispersed by a large amount of chloroformic acid methyl ester (4) at the bottom of the bubble column (3) by means of a spray nozzle (5). At the same time, cooled methanol preferably at a temperature of 5° to 25° C. (2) is introduced into this gas-in-liquid dispersion. The hydrogen chloride (6) formed flows out at the top of the bubble column. The reaction mixture (7) is fed, via an overflow, to the cooler (8), in which the heat of reaction is removed. The pump (9) circulates the chloroformic acid methyl ester, which is still charged with hydrogen chloride and phosgene. At partial stream of the ester (10) passes into the degassing column (11) at the bottom of which chloroformic acid methyl ester is vaporized (12) at about 71° C. Hydrogen chloride and phosgene flow out as the off-gas at the top of the column (13), via a cooler (14), in which the chloroformic acid methyl ester is condensed. A partial stream of chloroformic acid methyl ester is removed at the bottom (15) of the column (11).

Very pure chloroformic acid methyl ester is obtained in good yields by the process according to the invention. It is surprising that, with the aid of the process according to the invention, chloroformic acid methyl ester can be prepared with a small proportion of dimethyl carbonate and methyl chloride. Thus, in the process according to the invention, it is not necessary to extract, with water, the dimethyl carbonate obtained and to dry the chloroformic acid methyl ester. Working up of the water which contains dimethyl carbonate and is obtained as the effluent is also not required.

Moreover, the production of a fine gas-in-liquid dispersion from phosgene and chloroformic acid methyl ester and the simultaneous introduction of methanol into this dispersion result in the course of the reaction being surprisingly good. It is found, unexpectedly, that the efforts otherwise made to achieve short mixing times, and the use of liquid phosgene, are not decisive. Rather, the reaction time is independent of the mixing time.

It is also surprising that the subsequent reaction of the ester present with methanol is repressed to such an extent, although the gaseous dispersed phosgene is only available for reaction with methanol by virtue of its solubility in chloroformic acid methyl ester.

Surprisingly, the hydrogen chloride formed in the reaction does not react with the chloroformic acid methyl ester to give methyl chloride.

The particular advantage of the process according to the invention is that one can prepare chloroformic acid methyl ester in high purity with only slight excesses of phosgene in a known reactor (bubble column) without technical effort being required to achieve particularly short mixing times.

Chloroformic acid methyl ester is an intermediate product for plant protection agents and dyestuffs (Ullmann, volume 9, page 382 et seq. (1972)).

EXAMPLE 1

With reference to drawing 1, 325 kg/hour of phosgene (1) are finely dispersed by 12,000 kg/hour of chloroformic acid methyl ester (4) at the bottom of the bubble column (3) by means of a spray nozzle (5). At the same time, 103 kg/hour of cooled methanol (2) are introduced into this gas-in-liquid dispersion. The hydrogen chloride (6) formed flows out at the top of the bubble column. The reaction mixture (7) is fed, via an overflow, to the cooler (8), in which the heat of reaction is removed. The pump (9) circulates about 10 m$^3$/hour of chloroformic acid methyl ester, which is still partly charged with hydrogen chloride and phosgene. A part-stream of the ester (10) passes into the degassing column (11) at the bottom of which chloroformic acid methyl ester is vaporized (12) at about 71° C. Hydrogen chloride and phosgene flow out as the off-gas at the top of the column (13), via a cooler (14), in which the chloroformic acid methyl ester is condensed. A part-stream of 300 kg/hour of chloroformic acid methyl ester is removed at the bottom (15) of the column (11).

The content of dimethyl carbonate in the chloroformic acid methyl ester is less than 1% by weight.

What is claimed is:

1. In a process for the continuous preparation of chloroformic acid methyl ester by contacting phosgene with methanol at a temperature of up to 50° C. in a reactor which contains chloroformic acid methyl ester as the solvent and in which phosgene is dispersed, the improvement wherein gaseous phosgene is dispersed by already formed and circulated chloroformic acid methyl ester into the reaction chamber by means of a dispersing device, and at the same time methanol is introduced into the homogeneous gas-in-liquid dispersion.

2. A process according to claim 1 wherein the rise in temperature in the reaction chamber is controlled by the amount of chloroformic acid methyl ester circulating.

3. A process according to claim 1 wherein a bubble column is used as the reaction chamber.

4. A process according to claim 1 wherein the amount of circulating ester required for dispersing the phosgene permits a heating-up of the reaction mixture by at most 10° C.,

* * * * *